United States Patent [19]

Crook

[11] Patent Number: 5,344,421
[45] Date of Patent: Sep. 6, 1994

[54] APPARATUS AND METHOD FOR ADJUSTING A BONE PLATE

[75] Inventor: David F. Crook, Garland, Tex.

[73] Assignee: AMEI Technologies Inc., Wilmington, Del.

[21] Appl. No.: 92,801

[22] Filed: Jul. 16, 1993

[51] Int. Cl.⁵ .............................................. A61F 5/00
[52] U.S. Cl. ........................................ 606/61; 606/70; 606/71
[58] Field of Search ........................ 606/61, 69, 70, 71

[56] References Cited

U.S. PATENT DOCUMENTS

| | | |
|---|---|---|
| 3,604,414 | 9/1971 | Borges . |
| 3,648,691 | 3/1972 | Lumb et al. . |
| 3,693,616 | 9/1972 | Roaf et al. . |
| 4,611,581 | 9/1986 | Stefee . |
| 4,653,481 | 3/1987 | Howland et al. . |
| 4,655,199 | 4/1987 | Steffee . |
| 4,696,290 | 9/1987 | Steffee . |
| 4,743,260 | 5/1988 | Burton . |
| 4,771,767 | 9/1988 | Steffee . |
| 4,790,297 | 12/1988 | Luque . |
| 4,794,918 | 1/1989 | Wolter . |
| 4,836,196 | 6/1989 | Park et al. . |
| 4,887,595 | 12/1989 | Heinig et al. . |
| 4,913,134 | 4/1990 | Luque . |
| 4,950,269 | 8/1990 | Gaines, Jr. . |
| 4,957,496 | 9/1990 | Schmidt . |
| 4,957,497 | 9/1990 | Hoogland et al. . |
| 5,000,165 | 3/1991 | Watamabe . |
| 5,000,166 | 3/1991 | Karpf . |
| 5,002,542 | 3/1991 | Frigg . |
| 5,005,562 | 4/1991 | Cotrel . |
| 5,024,213 | 6/1991 | Asher et al. . |
| 5,030,220 | 7/1991 | Howland . |
| 5,041,113 | 8/1991 | Biedermann et al. . |
| 5,084,049 | 1/1992 | Asher et al. . |
| 5,092,893 | 3/1992 | Smith . |
| 5,108,395 | 4/1992 | Laurain . |
| 5,129,899 | 7/1992 | Small et al. . |
| 5,129,903 | 7/1992 | Luhr et al. . |
| 5,147,361 | 9/1992 | Ojima et al. . |
| 5,209,751 | 5/1993 | Farris et al. . |
| 5,234,431 | 8/1993 | Keller . |

FOREIGN PATENT DOCUMENTS

| | | | |
|---|---|---|---|
| 0286136 | 11/1970 | U.S.S.R. | 606/71 |
| 0860756 | 9/1981 | U.S.S.R. | 606/71 |
| 1695907 | 12/1991 | U.S.S.R. | 606/70 |
| 780652 | 6/1955 | United Kingdom | 606/61 |

*Primary Examiner*—Stephen C. Pellegrino
*Assistant Examiner*—Sonya C. Harris
*Attorney, Agent, or Firm*—Baker & Botts

[57] ABSTRACT

The present invention provides an adjustable bone plate assembly (10) comprising a plate (12) and washers (14). The plate (12) comprises an first surface (16) for engaging the bone, and a second surface (18) opposite the first surface (16). The plate (12) additionally comprises a plurality of slots (20) extending through the plate (12), and a plurality of protuberances (22) projecting from the second surface (18) of the plate (12). The washers (14) each comprise a first surface (24) having a plurality of indentations (28) for engaging the protuberances (22) of the plate (12) when a washer (14) is selectively placed over one of the plurality of slots (22).

19 Claims, 3 Drawing Sheets

APPARATUS AND METHOD FOR ADJUSTING A BONE PLATE

TECHNICAL FIELD OF THE INVENTION

The invention relates in general to the field of bone plates and, more particularly, to an adjustable bone plate and method for using the same.

BACKGROUND OF THE INVENTION

In fusing two vertebral bodies or setting a bone fracture, it is common practice to use a securing mechanism to hold the bone or vertebral bodies in place while the bone tissue fuses or heals. A commonly used securing mechanism is referred to as a bone plate. A bone plate aids the healing process by maintaining the fractured bone or vertebral bodies in a stable position. Once positioned, it is also desirable for the bone plate to remain securely fastened in place.

A bone plate is typically held in place by surgical screws or other appropriate devices inserted through openings in the bone plate. Because bone fractures and vertebrae structure vary from person-to-person and from bone-to-bone, a bone plate designed to allow variable placement of the surgical screws through the plate is desirable.

Prior adjustable bone plates have incorporated a two rack styled apparatus to allow for adjustable alignment of the plate and variable placement of screws in the bone tissue. A typical prior device comprises a lower plate having a toothed rack and an upper plate having an opposing toothed rack. The upper and lower plates may be placed together in various positions allowing variable placement of screws along the longitudinal axis of the bone plate. The rack on the upper plate is placed on the rack of the lower plate at the desired location and the appropriate screws are inserted through the plates and into the bone. Positive engagement between the opposing racks on the upper and lower plates provide some stability in the longitudinal direction of the bone plate. A major drawback to this type of system is that it provides, generally only stability and variable screw location in a longitudinal direction. Unfortunately, these prior art devices do not provide adequate stability or variability in screw placement in longitudinal, lateral or diagonal directions.

SUMMARY OF THE INVENTION

In accordance with the present invention, an adjustable bone plate is provided to substantially eliminate or reduce disadvantages and problems associated with prior adjustable bone plates.

The present invention provides an adjustable bone plate comprising a plate and a plurality of washers. The plate comprises a first surface for engaging the bone, and a second surface opposite the first surface. The plate additionally comprises a plurality of slots extending through the plate, and a first means for engaging the washers on the second surface of the plate adjacent to the slots. Each washer comprises a first surface having a second means for engaging the first engaging means of the plate when each washer is selectively placed over a selected slot. The first and second engaging means may comprise a plurality of protuberances projecting from one of the surfaces and a plurality of indentations in the other surface.

The plate is held securely to selected portions of a patient's body by inserting screws through the washers and plate while the protuberance - indentation interface provides lateral, longitudinal and diagonal stability for the plate. The plate allows for variable placement of the screws by allowing variable placement of the washer over selected slots of the plate.

A technical advantage of the present invention inheres in the fact that it uses means for engaging the washer and plate that provide stability in the lateral, longitudinal, and diagonal directions of the plate.

A further technical advantage of the present invention inheres in the fact that it provides a bone plate that is easily adjustable to be used in conjunction with a wide variety of bone and vertebrae structures.

BRIEF DESCRIPTION OF THE DRAWINGS

For a more complete understanding of the present invention, and the advantages thereof, reference is now made to the following description taken in conjunction with the accompanying drawings, in which.

DETAILED DESCRIPTION OF THE INVENTION

The preferred embodiments of the present invention and its advantages are best understood by referring to FIG. 1 through FIG. 4 of the drawings, like numerals being used for like and corresponding parts of the various drawings.

Figure 1:
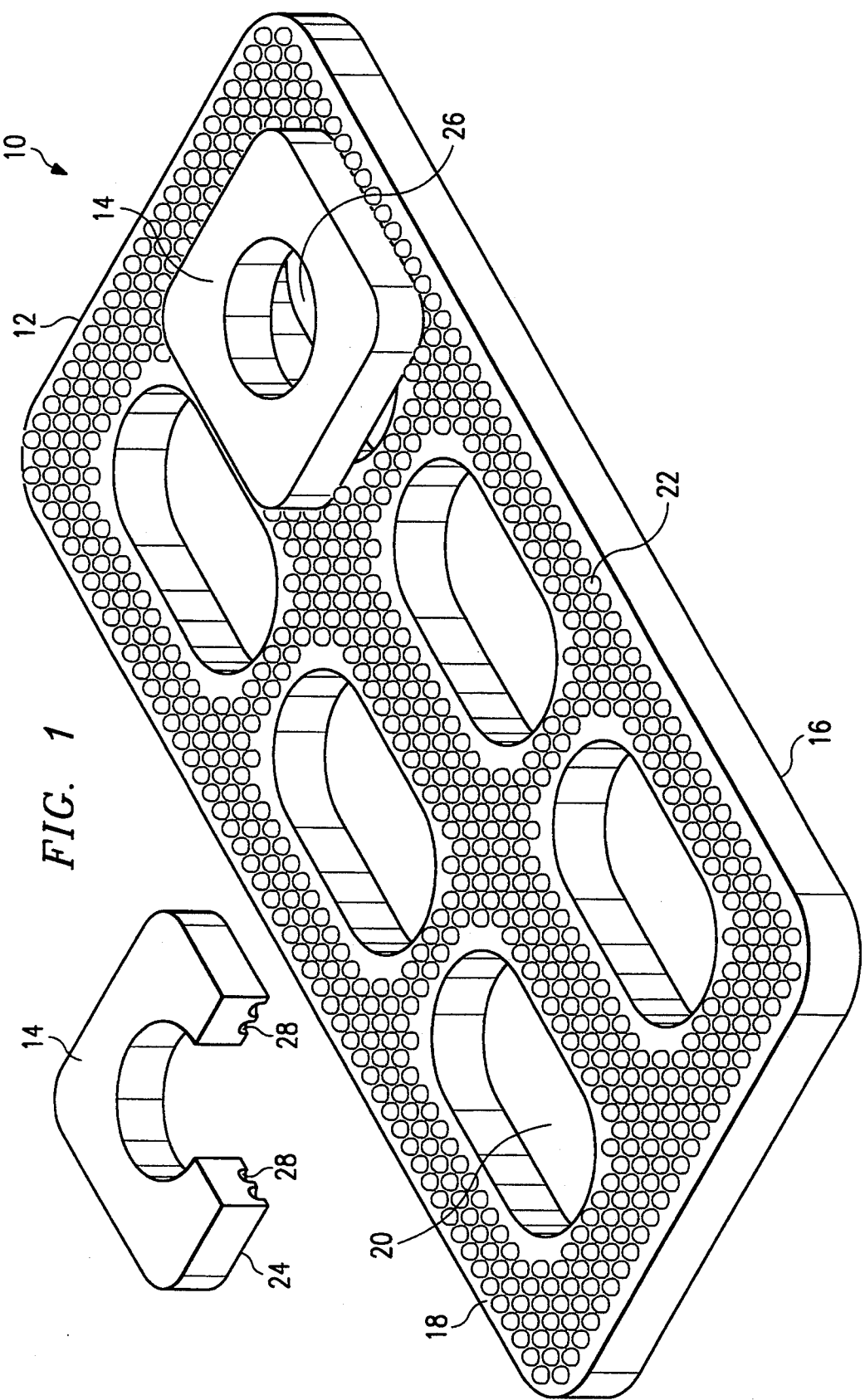
FIG. 1 is a isometric drawing with portions broken away of an embodiment of an adjustable bone plate and washer constructed according to the teachings of the present invention.
Figure 4:
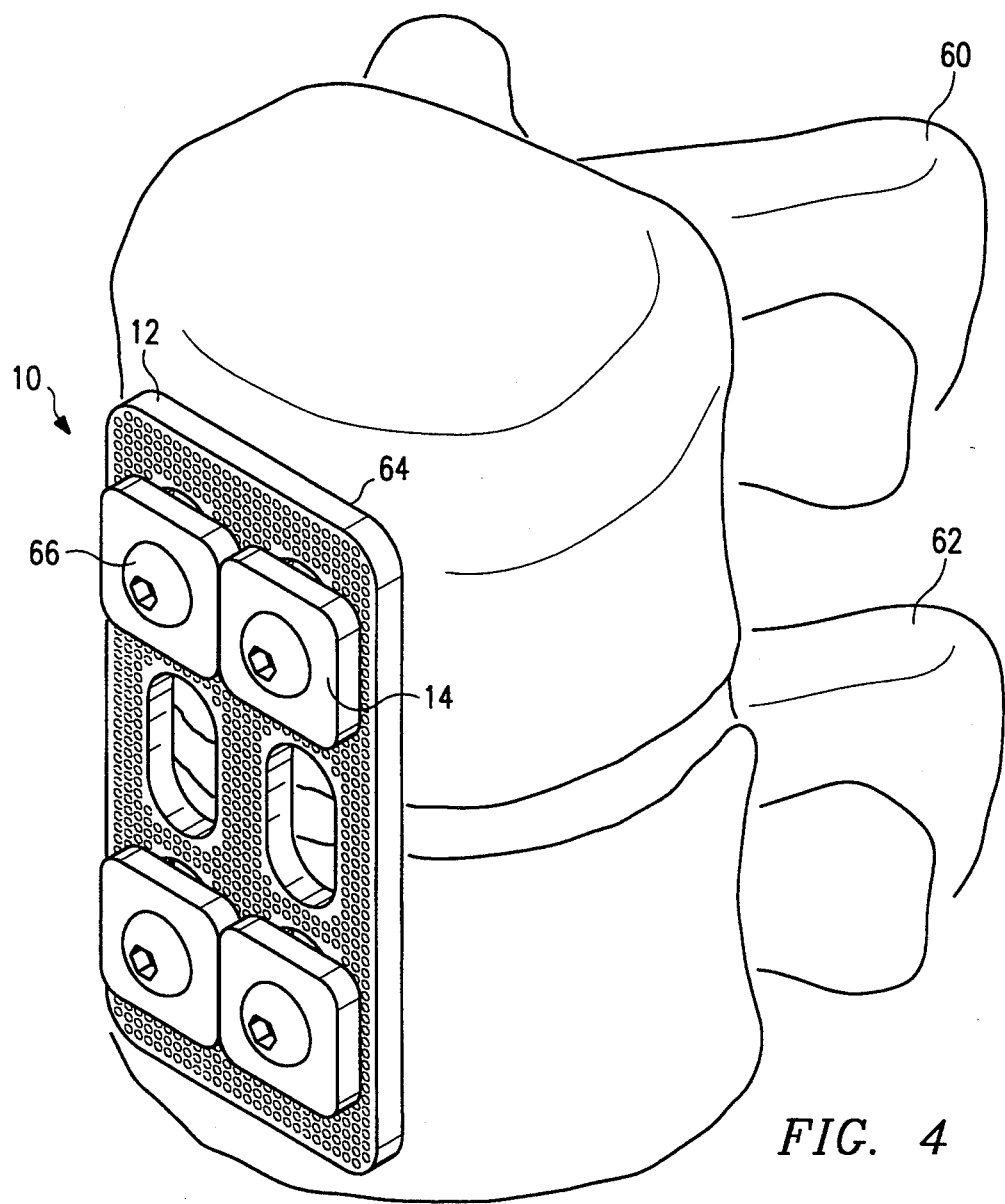
FIG. 4 is a schematic illustration of an adjustable bone plate constructed and connected to two vertebral bodies according to the teachings of the present invention.

FIG. 1 illustrates one embodiment of an adjustable bone plate assembly indicated generally at 10. Assembly 10 comprises a bone plate 12 and washers 14. In use, an appropriate number of washers 14 are used with plate 12 to accommodate an appropriate number of screws as shown in FIG. 4 for a particular bone or tissue application.

Figure 2:
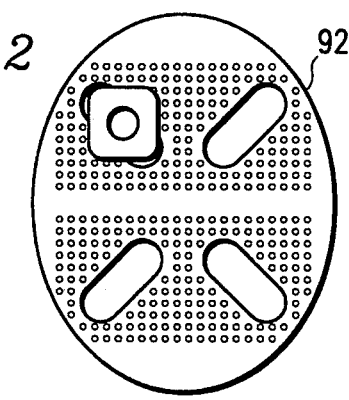
FIG. 2 is a top view of another embodiment of an adjustable bone plate and washer constructed according to the teachings of the present invention.

Plate 12 comprises a substantially rectangular plate having a length on the order of approximately 2.2 inches, a width on the order of approximately 1.1 inches, and a thickness on the order of 0.1 inch. Alternatively, plate 12 may comprise a square, a V-shape or other appropriate shape for securing a bone fracture in place. For example, as shown in FIG. 2, plate 92 may comprise an elliptical shape. Additionally, the size of plate 12 may be varied to accommodate use with different bone fusion applications. For example, plate 12 may be substantially longer than 2.2 inches when used for fusing large fractures in long bones. Plate 12 may comprise, for example, a conventional biocompatible material such as Ti 6A14V, low carbon stainless steel, or other suitable implant material. Plate 12 comprises a first surface 16 and a second surface 18.

Plate 12 further comprises six substantially rectangular slots 20 and a plurality of protuberances 22. Slots 20 are oriented in pairs with one slot 20 on each side of a longitudinal axis of plate 12. Slots 20 extend through plate 12 from first surface 16 to second surface 18. The number, orientation, and shape of slots 20 may be varied to provide other arrangements suitable for appropriate bone fusion treatments. For example, slots 20 may be oriented parallel or perpendicular to the longitudinal axis of plate 12. Alternatively, slots 20 may be oriented along a diagonal as shown in FIG. 2 for plate 92. Slots 20 are suitably positioned in plate 12 to allow proper placement of screws or other securing devices such that plate 12 may be used in a wide range of bone fusion operations by simple adjustment of the location of washers 14 over slots 20.

Protuberances 22 project from second surface 18 of plate 12. Protuberances 22 may be suitably spaced apart to provide a means for engaging and securely holding washers 14 in place on plate 12.

Washers 14 comprise substantially square washers, each having a first surface 24. Alternatively, washers 14 may comprise a substantially circular or other suitable shape for holding a screw extending through a slot 20 securely in place. Additionally, washers 14 each comprise an aperture 26 therethrough for receiving a screw as shown in FIG. 4. Alternatively, washers 14 may each comprise multiple apertures 26 to allow more than one screw to be inserted through each washer 14 and its associated slot 20. Washers 14 may comprise, for example, a biocompatible material such as Ti 6A14V, low carbon stainless steel, or other suitable implant material. Finally, washers 14 each comprise a plurality of indentations 28 in first surface 24. Indentations 28 are appropriately spaced to be able to positively engage protuberances 22 of plate 12.

In operation, a washer 14 is selectively placed on second surface 18 of plate 12 over a selected slots 20 such that a portion of protuberances 22 engage indentations 28 to securely hold washer 14 in an appropriate location on plate 12. The physician implanting apparatus 10 in a particular application will determine the appropriate number of washers 14 to be used and the appropriate location for those washers over slots 20 of plate 12. An example of the implementation of assembly 10 is described below with respect to FIG. 4.

Figure 3:
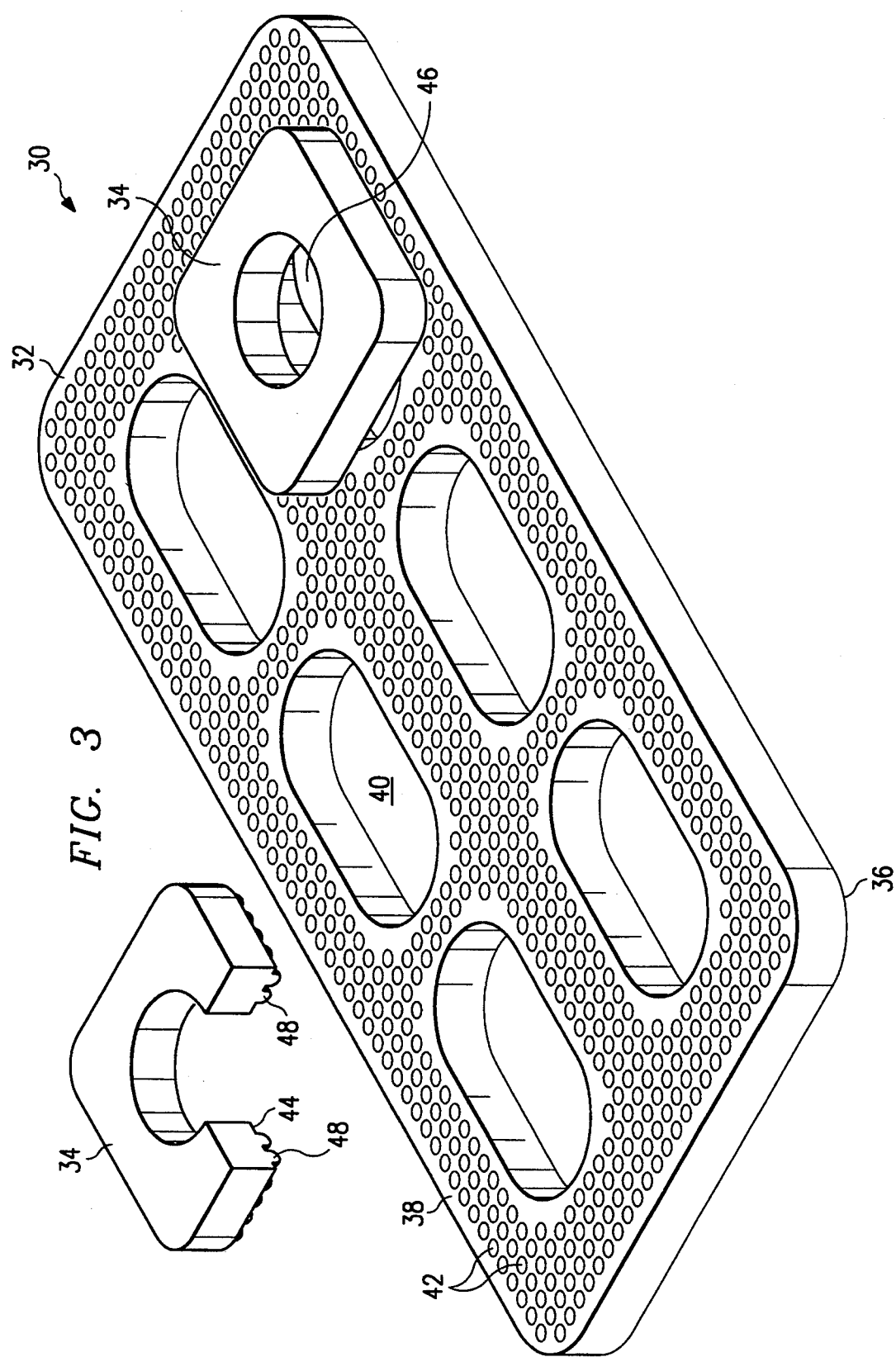
FIG. 3 is a isometric drawing with portions broken away of another embodiment of an adjustable bone plate and washer constructed according to the teachings of the present invention.

FIG. 3 illustrates another embodiment of an adjustable bone plate assembly indicated generally at 30. Assembly 30 comprises a bone plate 32 and washers 34. In use, an appropriate number of washers 34 are used with plate 32 to accommodate an appropriate number of screws as shown in FIG. 4 with respect to assembly 10 for a particular bone tissue fusion application.

Plate 32 comprises a substantially rectangular plate having a length on the order of approximately 2.2 inches, a width on the order of approximately 1.1 inches, and a thickness on the order of 0.1 inch. Alternatively, plate 32 may comprise a square, an X-shape or other appropriate shape for securing a bone fracture in place. For example, as with plate 92 shown in FIG. 2, plate 32 may also comprise an elliptical shape. Additionally, the size of plate 32 may be varied to accommodate use with different bone fusion applications. For example, plate 32 may be substantially longer than 2.2 inches when used for fusing large fractures in long bones. Plate 32 may comprise, for example, a conventional biocompatible material such as Ti 6A14V, low carbon stainless steel, or other suitable implant material. Plate 32 comprises a first surface 36 and a second surface 38.

Plate 32 further comprises six substantially rectangular slots 40 and a plurality of indentations 42 in second surface 38. Slots 40 are oriented in pairs with one slot 40 on each side of a longitudinal axis of plate 32. Slots 40 extend through plate 32 from first surface 36 to second surface 38. The number, orientation, and shape of slots 40 may be varied to provide other arrangements suitable for appropriate bone fusion treatments. For example, slots 40 may be oriented parallel or perpendicular to the longitudinal axis of plate 32. Alternatively, plate 32, as with plate 92 of FIG. 2, may comprise 4 slots 40 oriented along a diagonal. Slots 40 are suitably positioned in plate 32 to allow proper placement of screws or other securing devices such that plate 32 may be used in a wide range of bone fusion operations by simple adjustment of the location of washers 34 over slots 40. Indentations 42 may be suitably spaced apart to provide a means for engaging and securely holding washers 34 in place on plate 32.

Washers 34 comprise substantially square washers, each having a first surface 44. Alternatively, washers 44 may comprise a substantially circular or other suitable shape for holding a screw extending through a slot 40 securely in place. Additionally, washers 34 each comprise an aperture 46 therethrough for receiving a screw. Alternatively, washers 34 may each comprise multiple apertures 46 to allow more than one screw to be inserted through each washer 34. Washers 34 may comprise, for example, a biocompatible material such as Ti 6A14V, low carbon stainless steel, or other suitable implant material. Finally, washers 34 each comprise a plurality of protuberances 48 projecting from first surface 44. Protuberances 48 are appropriately spaced to be able to positively engage indentations 42 of plate 32.

In operation, a washer 34 is selectively placed on second surface 38 of plate 32 over one of slots 40 such that a portion of protuberances 48 engage indentations 42 to securely hold washer 34 in an appropriate location on plate 32. The physician implanting apparatus 30 in a particular application will determine the appropriate number of washers 34 to be used and the appropriate location for those washers over slots 40 of plate 32.

FIG. 4 illustrates adjustable bone plate assembly 10 connected to vertebral bodies 60 and 62. It is noted that adjustable bone plate assembly 10 is used in FIG. 4 for illustration purposes only. Adjustable bone plate assembly 30 may be similarly attached to vertebral bodies 60 and 62. Additionally, it is noted that assembly 10 and assembly 30 may be used with a bone fracture as well as with fusion of vertebrae.

In fusing vertebral bodies 60 and 62, the physician implementing assembly 10 places first surface 16 of plate 12 in contact with surface 64 of vertebral bodies 60 and 62 in an appropriate location to aid in the fusing of vertebral bodies 60 and 62. The physician also selectively places washers 14 over slots 20 of plate 12 in appropriate positions to allow assembly 10 to be securely connected to vertebral bodies 60 and 62. Washers 14 are securely held in place in both lateral and longitudinal directions by indentations 28 positively engaging a plurality of protuberances 22 of plate 12. A screw 66 is inserted through aperture 26 of each washer 14 to secure assembly 10 to vertebral bodies 60 and 62. It is noted that a particular application of assembly 10 may not require insertion of a screw 66 through every slot 20. The decision as to how many washers and which slots are to be used is left to the medical judgment of the implementing physician.

Although the present invention and its advantages have been described in detail, substitutions and alterations can be made without departing from the spirit and scope of the invention as defined by the following claims.

I claim:

1. An adjustable bone plate assembly, comprising:
   a plate having a first surface for engaging a selected portion of a patient's body, a second surface opposite said first surface, and a plurality of slots extending through said plate;
   a plurality of washers, said washers having a first surface;
   first means disposed on said second surface of said plate for engaging said washers; and
   second means disposed on said first surface of said washer for engaging said first means on said plate, wherein said washers are selectively placed on said second surface of said plate over one of said plurality of slots such that said first and second means are operable to prevent both lateral and longitudinal movement of said washer on said plate.

2. The adjustable bone plate assembly of claim 1, wherein said first engaging means comprises a plurality of protuberances projecting from said second surface of said plate and said second engaging means comprises a plurality of indentations in said first surface of said washer.

3. The adjustable bone plate assembly of claim 2, wherein said plate comprises a substantially rectangular plate having a length of approximately 2 inches, a width of approximately 1 inch, and a thickness of approximately 0.1 inch.

4. The adjustable bone plate assembly of claim 2, wherein said plate comprises a bio-compatible material.

5. The adjustable bone plate assembly of claim 2, wherein said plurality of slots comprises substantially rectangular slots extending along a longitudinal axis of said plate.

6. The adjustable bone plate assembly of claim 5, wherein said plurality of slots comprises pairs of slots located on opposite sides of said longitudinal axis of said plate.

7. The adjustable bone plate assembly of claim 2, wherein said washer comprises a substantially square washer having a circular aperture therethrough for receiving a bone screw.

8. The adjustable bone plate assembly of claim 2, further comprising a bone screw sized to be inserted through said washer for securely fastening said adjustable bone plate to a selected portion of a patient's body.

9. The adjustable bone plate assembly of claim 1, wherein said first engaging means comprises a plurality of indentations in said second surface of said plate and said second engaging means comprises a plurality of protuberances projecting from said first surface of said washer.

10. The adjustable bone plate assembly of claim 9, wherein said plate comprises a substantially rectangular plate having a length of approximately 2 inches, a width of approximately 1 inch, and a thickness of approximately 0.1 inch.

11. The adjustable bone plate assembly of claim 9, wherein said plate and washer comprise bio-compatible material.

12. The adjustable bone plate assembly of claim 9, wherein said plurality of slots comprises substantially rectangular slots extending along a longitudinal axis of said plate.

13. The adjustable bone plate assembly of claim 12, wherein said plurality of slots comprises slot pairs located on opposite sides of said longitudinal axis of said plate.

14. The adjustable bone plate assembly of claim 9, further comprising an elliptical plate.

15. The adjustable bone plate assembly of claim 9, wherein said washer comprises a substantially square washer having a circular aperture therethrough for receiving a bone screw.

16. The adjustable bone plate assembly of claim 9, and further comprising a bone screw sized to be inserted through said washer for securely fastening said adjustable bone plate to a selected portion of a patient's body.

17. A method for securely implanting an adjustable bone plate assembly, comprising the steps of:
   placing a first surface of a plate on a bone, the plate having a second surface opposite the first surface, and a plurality of slots extending through the plate;
   placing a washer on the plate adjacent the slots, the washer having a first surface;
   engaging a first means for engaging a washer disposed on the second surface of the plate with a second means for engaging the washer disposed on the first surface of the washer such that the washer is securely held in place over one of the plurality of slots, the first and second means operable to prevent both lateral and longitudinal movements of the washer on the plate; and
   inserting a screw through an aperture of the washer, through the slot of the plate, and into the bone to hold the adjustable bone plate assembly in place.

18. The method of claim 17, wherein said step of engaging comprises the step of engaging a plurality of protuberances projecting from the first surface of the washer with a plurality of indentations in the second surface of the plate such that the washer is securely held in place over one of the plurality of slots.

19. The method of claim 17, wherein said step of engaging comprises the step of engaging a plurality of protuberances projecting from the second surface of the plate with a plurality of indentations in the first surface of the washer such that the washer is securely held in place over one of the plurality of slots.

* * * * *